US009380987B2

(12) United States Patent
Kojima et al.

(10) Patent No.: US 9,380,987 B2
(45) Date of Patent: Jul. 5, 2016

(54) X-RAY CT DEVICE

(71) Applicant: HITACHI MEDICAL CORPORATION, Chiyoda-ku, Tokyo (JP)

(72) Inventors: Shinichi Kojima, Tokyo (JP); Fumito Watanabe, Tokyo (JP); Hironori Ueki; Yasutaka Konno, Tokyo (JP); Yushi Tsubota, Tokyo (JP)

(73) Assignee: Hitachi Medical Corporation, Tokyo (JP)

(*) Notice: Subject to any disclaimer, the term of this patent is extended or adjusted under 35 U.S.C. 154(b) by 219 days.

(21) Appl. No.: 14/364,257

(22) PCT Filed: Dec. 12, 2012

(86) PCT No.: PCT/JP2012/082250
§ 371 (c)(1),
(2) Date: Jun. 10, 2014

(87) PCT Pub. No.: WO2013/089154
PCT Pub. Date: Jun. 20, 2013

(65) Prior Publication Data
US 2014/0321610 A1     Oct. 30, 2014

(30) Foreign Application Priority Data

Dec. 12, 2011 (JP) .................. 2011-270844

(51) Int. Cl.
*A61B 6/00* (2006.01)
*A61B 6/03* (2006.01)
(Continued)

(52) U.S. Cl.
CPC ............. *A61B 6/4266* (2013.01); *A61B 6/032* (2013.01); *A61B 6/4021* (2013.01);
(Continued)

(58) Field of Classification Search
CPC .... A61B 6/4266; A61B 6/032; A61B 6/4208; A61B 6/4021; A61B 6/4291; A61B 6/5205; A61B 6/467; A61B 6/5282; G01T 1/243
USPC ............................. 378/4–20, 98.8, 145, 147
See application file for complete search history.

(56) References Cited

U.S. PATENT DOCUMENTS 4,731,534 A * 3/1988 Klein .................... G01T 1/1644
250/366
5,373,162 A   12/1994 Akai
(Continued)

FOREIGN PATENT DOCUMENTS

CN    101002108 A    7/2007
CN    101413905 A    4/2009
(Continued)

OTHER PUBLICATIONS

Chinese Office Action received in corresponding Chinese Application No. 201280061304.8 dated Oct. 28, 2015.

*Primary Examiner* — Courtney Thomas
(74) *Attorney, Agent, or Firm* — Mattingly & Malur, PC

(57) ABSTRACT

In order to suppress reduction in sensitivity when acquiring high-resolution data, an X-ray CT device is provided with an X-ray source that irradiates a patient with X-rays, and an X-ray detector that detects the X-rays. The X-ray detector includes a plurality of detection elements (scintillators and photodiodes) arrayed in a first direction, and a plurality of separators that separate the detection elements arrayed in the first direction respectively from each other. The separators each have a first-direction width which is a width in the first direction, first-direction widths of some separators each arrayed every predetermined number of separators being different from first-direction widths of the other separators.

15 Claims, 14 Drawing Sheets

(51) Int. Cl.
*G01T 1/20* (2006.01)
*G01T 1/24* (2006.01)

(52) U.S. Cl.
CPC ............ *A61B 6/4208* (2013.01); *A61B 6/4291* (2013.01); *A61B 6/5205* (2013.01); *G01T 1/2002* (2013.01); *G01T 1/243* (2013.01); *A61B 6/467* (2013.01); *A61B 6/5282* (2013.01); *A61B 6/54* (2013.01)

(56) References Cited

U.S. PATENT DOCUMENTS

| 6,215,843 | B1 | 4/2001 | Saito et al. |
| 6,393,092 | B1 * | 5/2002 | Yoshida ................ G01T 1/2018 250/370.09 |
| 6,895,080 | B2 | 5/2005 | Baba et al. |
| 2005/0135563 | A1 * | 6/2005 | Hoffman ................ A61B 6/032 378/154 |
| 2008/0093559 | A1 | 4/2008 | Dorschieid et al. |
| 2008/0101542 | A1 * | 5/2008 | Ikhlef .................... G21K 1/025 378/147 |
| 2010/0091947 | A1 | 4/2010 | Niu et al. |

FOREIGN PATENT DOCUMENTS

| DE | 3028996 A1 | 3/1982 |
| JP | 10-127617 A | 5/1998 |
| JP | 11-295430 A | 10/1999 |
| JP | 2000-093418 A | 4/2000 |
| JP | 2001-42044 A | 2/2001 |
| JP | 2001-46364 A | 2/2001 |
| JP | 2002-022678 A | 2/2002 |
| JP | 2009-118943 A | 6/2009 |

* cited by examiner

X-RAY CT DEVICE

TECHNICAL FIELD

The present invention relates to an X-ray CT device, more particularly, to an X-ray CT device that has a structure adapted to suppress reduction in sensitivity when acquiring high-resolution data.

BACKGROUND ART

An X-ray CT device is a device for reconstructing a difference of X-ray absorptance within a patient, using data processing system, as an image. The X-ray CT device is provided with an X-ray source that irradiates a patient with X-rays, and an X-ray detector for imaging a patient that detects the X-rays transmitted through the patient, at a position opposed to the X-ray source, and images a difference of X-ray absorptance within the patient based on projection data in multiple directions acquired by carrying out image acquisition while rotating around the patient.

The X-ray detector of the X-ray CT device includes a plurality of detection elements. X-rays incident on the detection element are first converted by a scintillator in the detection element into photons (fluorescence). The converted photons are subject to photoelectric conversion by a photodiode in the same detection element and then processed as an electric signal in a circuit of subsequent stage. However, X-rays not incident on the detection element do not become an electric signal. For this reason, the X-ray detector of the X-ray CT device is configured to arrange as many as possible of the detection elements to reduce the part other than the detection elements, thereby enhancing sensitivity to X-rays and reducing ineffective radiation exposure.

Thus, the X-ray detector of the X-ray CT device is constituted by the plurality of detection elements, but as a result of communication of signals between the detection elements, an event called "crosstalk" by which the image blurs may occur. To cope with this, the X-ray detector is provided with separators interposed between the detection elements respectively, and reduces crosstalk by the separators. Crosstalk blocking capability of the separator depends on the thickness thereof, and making the separator thicker enhances the crosstalk blocking capability. On the other hand, since the separator cannot detect X-rays, the sensitivity of the X-ray detector is reduced with the separator being made thicker, to thereby increase ineffective radiation exposure.

Moreover, the X-ray detector of the X-ray CT device is provided with collimators on the side of the X-ray source in order to prevent X-rays scattered within the patient (scattered radiation) from entering the detection elements. Since shadow by the collimators also causes reduction in sensitivity of the X-ray detector, for example, a method of disposing the collimators on the separators to suppress the reduction in sensitivity to the minimum is adopted. Moreover, since the amount of X-rays incident on the detection elements varies depending on error of design of the collimators, for example, a method of segmentalizing detection elements to use only the part which receives X-rays (for example, see Patent Literature 1), a method of making the separators thicker than the collimators to absorb a margin of the error, and the like, are known.

Moreover, Patent Literature 2 discloses an X-ray measuring device in which an X-ray shielding member (collimator) is disposed so that a line passing on an X-ray focal spot and the center of a width of a blind part (separator) of a detection element passes on the center of a width of the X-ray shielding member, and in which a pitch in the array of X-ray shielding members is an integer multiple of two or larger of a pitch in the array of blind parts of detection elements.

CITATION LIST

Patent Literature

Patent Literature 1: Japanese Patent Application Publication No. 2000-93418
Patent Literature 2: Japanese Patent Application Publication No. 2002-22678

SUMMARY OF INVENTION

Technical Problem

As described above, as for the X-ray detector of the X-ray CT device, its sensitivity and resolution vary depending on the respective positions and sizes of the detection elements, the separators and the collimators. Although an X-ray CT device whose sensitivity and resolution are both excellent is ideally desirable, the X-ray CT device generally has a relationship of tradeoff between sensitivity and resolution.

However, in an examination using an X-ray CT device, the sensitivity is very significant. Moreover, even in the case of improving resolution, improvement in the sensitivity is demanded. This is because reduction in sensitivity increases image noises to make it impossible to obtain an intended resolution. For example, when respective resolutions in two directions in a two-dimensional image are set to ½ (for example, resolution of 1 mm is enhanced to resolution of 0.5 mm), it must acquire four times as much as the data to obtain images of the same statistical noise as that obtained at the resolution of 1 mm, at the resolution of 0.5 mm. For this reason, a structure by which reduction in sensitivity is suppressed to the extent possible when acquiring high-resolution data has been needed.

In view of this, the present invention makes it an object thereof to provide an X-ray CT device that has a structure adapted to suppress reduction in sensitivity when acquiring high-resolution data.

Solution to Problem

In order to solve the problem, the present invention provides an X-ray CT device provided with an X-ray source that irradiates a patient with X-rays, and an X-ray detector that detects the X-rays, the X-ray detector including: a plurality of detection elements arrayed in a first direction; and a plurality of separators that separate the detection elements arrayed in the first direction respectively from each other, the separators each having a first-direction width which is a width in the first direction, first-direction widths of some separators each arrayed every predetermined number of separators being different from first-direction widths of the other separators.

Advantageous Effects of Invention

According to the present invention, it is possible to provide an X-ray CT device that has a structure adapted to suppress reduction in sensitivity when acquiring high-resolution data.

BRIEF DESCRIPTION OF DRAWINGS

FIGS. 2A and 2B are enlarged schematic views enlarging part of an X-ray detector according to the first embodiment, in which FIG. 2A is a schematic view when viewing the X-ray detector in a slice direction, and FIG. 2B is a schematic view when viewing the X-ray detector in an X-ray irradiation direction.

FIGS. 9A to 9C are enlarged schematic views enlarging part of an X-ray detector, in which FIG. 9A is a schematic view of the X-ray detector which is in rotation, FIG. 9B is a schematic view when viewing an X-ray detector according to a first modified example in a slice direction, and FIG. 9C is a schematic view when viewing the X-ray detector according to the first modified example in an X-ray irradiation direction.

DESCRIPTION OF EMBODIMENTS

Hereinafter, the mode for carrying out the present invention (hereinafter referred to as "embodiment") will be described in detail with reference to the drawings when necessary. Note that, in each figure, the common part is given the same sign and duplicate description thereof is omitted.

First Embodiment

General Configuration of X-Ray CT Device 100

Figure 1:
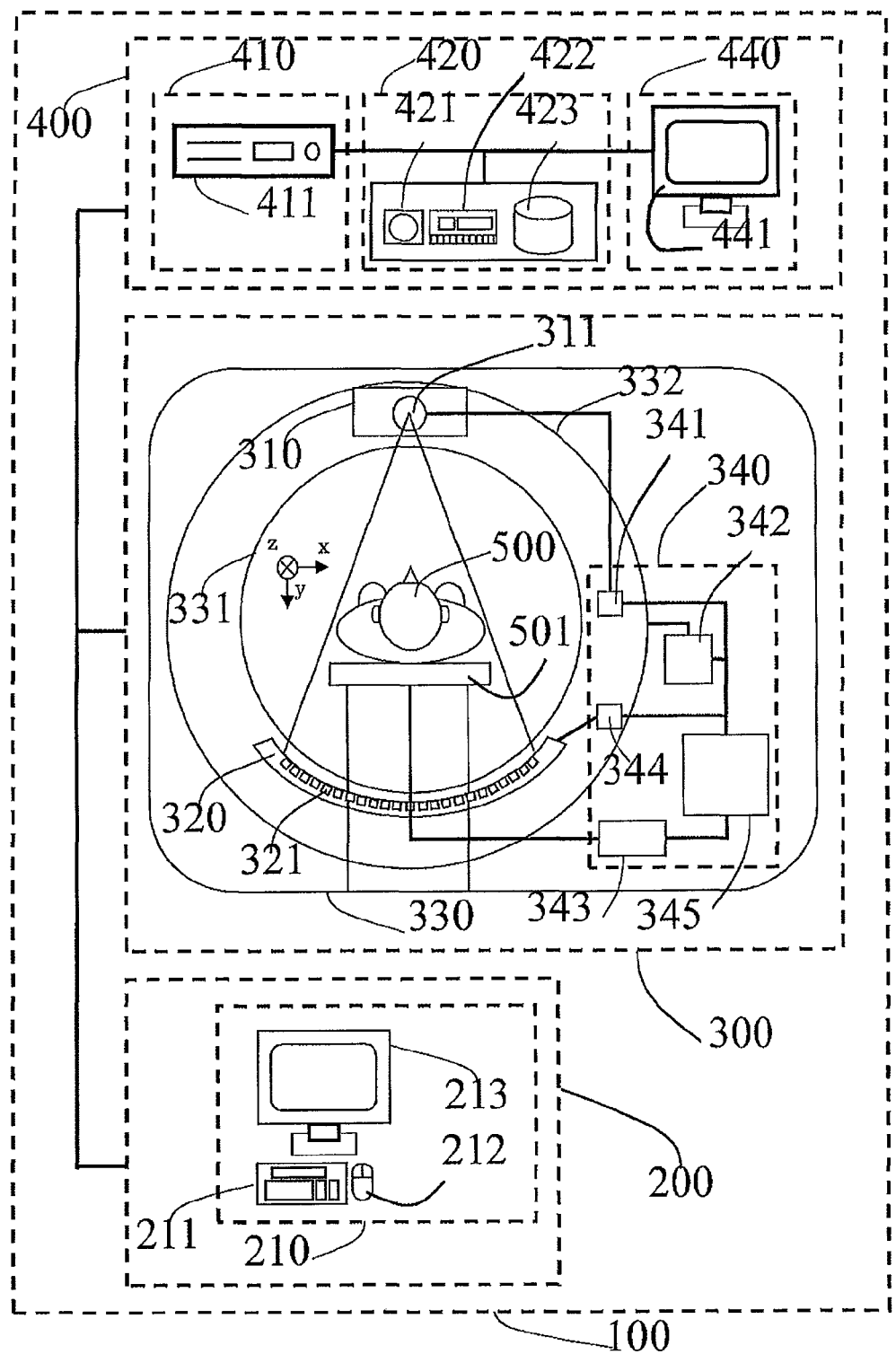
FIG. 1 is an explanatory diagram illustrating a configuration of an X-ray CT device according to a first embodiment.

FIG. 1 is an explanatory diagram illustrating a configuration of the X-ray CT device 100 according to a first embodiment. In the description below, the x-axis direction in FIG. 1 is defined as a channel direction, the y-axis direction is defined as an X-ray irradiation direction, and the z-axis direction is defined as a slice direction. FIG. 1 illustrates the X-ray CT device 100 as viewed from the body-axis direction (slice direction: z-axis direction) of a patient 500.

The X-ray CT device 100 is constituted by an input unit 200, a scanning unit 300 and an image generation unit 400. Note that the input unit 200 and the image generation unit 400 do not necessarily need to be integral with the X-ray CT device 100. For example, by another device connected via a network to the X-ray CT device 100, the operation thereof may be realized. Moreover, a device having both functions of the image generation unit 400 and the input unit 200 may be used.

The input unit 200 includes a scanning conditions input unit 210, which is constituted by a keyboard 211, a mouse 212 and a monitor 213 and accepts inputting of scanning conditions from an operator. When the monitor 213 has a function of touch panel, the touch panel may be used as the scanning conditions input unit 210.

The scanning unit 300 is constituted by an X-ray generation unit 310, an X-ray detection unit 320, a gantry 330, a scanning control unit 340, and a patient-carrying table 501.

The X-ray generation unit 310 is provided with an X-ray tube 311 which is an X-ray source for irradiating X-rays.

The X-ray detection unit 320 is provided with an X-ray detector 321. Note that details of the X-ray detector 321 will be described later with reference to FIGS. 2A and 2B.

Provided in the center of the gantry 330 is a circular bore 331 for disposing therein the patient 500 and the patient-carrying table 501. Provided in the gantry 330 are a rotating plate 332 that mounts thereon the X-ray generation unit 310 (X-ray tube 311) and the X-ray detection unit 320 (X-ray detector 321), and a rotary drive mechanism (not shown) for rotating the rotating plate 332. Moreover, provided in the patient-carrying table 501 is a table drive mechanism (not shown) for adjusting a position of the patient 500 relative to the gantry 330.

The scanning control unit 340 is constituted by an X-ray controller 341, a gantry controller 342, a table controller 343, a detector controller 344 and an integrated controller 345. The X-ray controller 341 controls the X-ray tube 311. The gantry controller 342 controls the rotary drive mechanism (not shown) of the rotating plate 332. The table controller 343 controls the table drive mechanism (not shown) of the patient-carrying table 501. The detector controller 344 controls scanning of the X-ray detector 321. The integrated controller 345 controls the flow of respective operations of the X-ray controller 341, the gantry controller 342, the table controller 343 and the detector controller 344.

Note that in the present embodiment, a distance between an X-ray originating point of the X-ray tube 311 and an X-ray input plane of the X-ray detector 321 is set to, for example, 1000 mm. Also, a diameter of the opening 331 of the gantry 330 is set to, for example, 700 mm.

A required time for rotation of the rotating plate 332 depends on parameters which the operator inputs using the scanning conditions input unit 210. In the present embodiment, the required time for rotation is set to, for example, 1.0 s/turn. Moreover, the number of times of scanning by the scanning unit 300 in one rotation is set to, for example, 900 times, and one scanning is carried out every rotation of 0.4 degrees of the rotating plate 332.

Note that parameters at the scanning by the X-ray CT device 100 are not limited to these values and can be changed variously according to the configuration of the X-ray CT device 100.

The image generation unit 400 is provided with a signal acquisition unit 410, a data processing unit 420 and an image display unit 440, and carries out various processings for projection data acquired by the scanning unit 300 to output the processed data as image data. The signal acquisition unit 410 includes a DAS (Data Acquisition System) 411. The DAS 411 converts X-ray detection results by the X-ray detector 321 into digital signals.

The data processing unit 420 is constituted by a CPU (Central Processing Unit) 421, a memory 422 and a HDD (Hard Disk Drive) device 423. The CPU 421 and the memory 422 perform various processings such as calculation for correction, processing for reconstruction of images and the like, by running and expanding predetermined programs. The HDD device 423 carries out storing, inputting and outputting of data. The image display unit 440 is provided with an image display monitor 441 such as a liquid crystal display, a CRT (Cathode Ray Tube) and the like, and displays reconstructed images.

<X-Ray Detector 321>

Next, a detailed configuration of the X-ray detector 321 will be described with reference to FIGS. 2A and 2B.

Figure 2A:
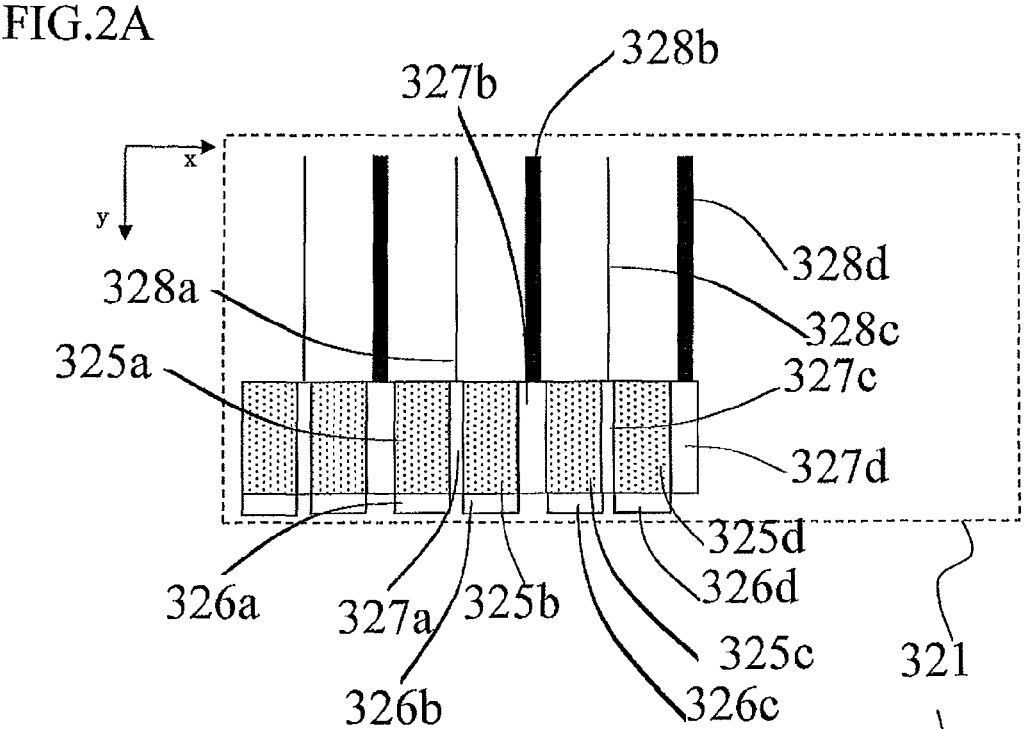
Figure 2B:
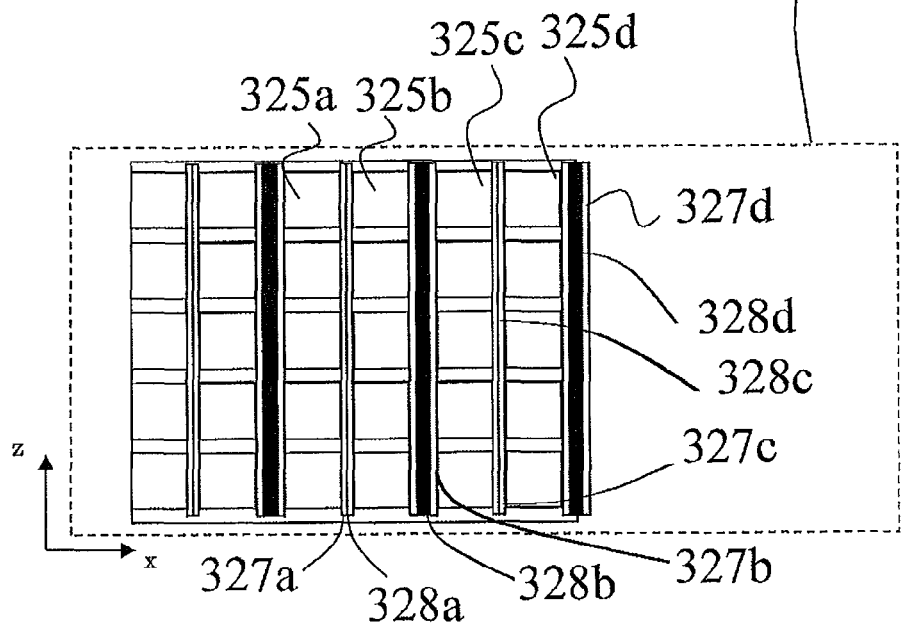

FIGS. 2A and 2B are enlarged views enlarging part of the X-ray detector 321 according to the first embodiment, in which FIG. 2A is a schematic view when viewing the X-ray detector 321 in the z-direction (the slice direction, the body-axis direction of the patient 500), and FIG. 2B is a schematic view when viewing the X-ray detector 321 in the y-direction (the X-ray irradiation direction).

As illustrated in FIGS. 2A and 2B, the X-ray detector 321 is constituted by scintillators 325 (325a to 325d) each of which is an element that receives X-rays or ionizing radiation to produce fluorescence, photodiodes 326 (326a to 326d) each of which is an element that converts light such as fluorescence into electricity, separators 327 (327a to 327d) that separate the scintillators 325 from each other, and collimators 328 (328a to 328d) that restrict the incident direction of X-rays to the scintillator 325. More specifically, the scintillators 325, the photodiodes 326, the separators 327 and the collimators 328 are arrayed in the rotating direction of the X-ray detector 321.

Here, the X-ray detector 321 is described as a scintillation detector which is constituted by detection elements consisting of the scintillators 325 and the photodiodes 326. In this case, reflective material is often used as the separators 327.

Note that the X-ray detector 321 is not limited to the scintillation detector and may be an X-ray detector constituted by detection elements using the other system. For example, the X-ray detector 321 may be a semiconductor detector. When such a semiconductor detector is used as the X-ray detector 321, gap or insulating material is often used as the separators 327.

The X-ray detector 321 has a configuration in which multiple scintillators 325 are arrayed in the form of a circular arc at an equal distance from the X-ray originating point of the X-ray tube 311, and the number of elements in the x-direction (the number of channels) is, e.g., 1000. A width in the channel direction of each scintillator 325 is, e.g., 1 mm. Note that, in order to facilitate manufacturing, a configuration may be used which is obtained by making a plurality of detectors (detector modules) with flat surface and arranging the modules so that central portions of their flat surfaces form an arc to thereby array the modules in the form of a quasi-arc.

As shown in FIGS. 2A and 2B, the detection elements consisting of the scintillators 325 and the photodiodes 326 are all configured to have the same size, but a thickness of each separator 327 and a thickness of each collimator 328 are periodically different, respectively. Here, the thickness is the width in the x-direction (channel direction).

Specifically, as shown in FIG. 2A, the separator 327a and the separator 327c have a relatively thin structure, and the separator 327b and the separator 327d have a relatively thick structure. Namely, the relatively thin separator 327 and the relatively thick separator 327 are arrayed periodically (every one separator (with two pitches) in FIGS. 2A and 2B). Note that the central positions in the thickness direction of the separators 327 are located at equal spaces. On the other hand, the central positions in the thickness direction of the scintillators 325 are periodically (specifically, with two pitches) different from each other.

Moreover, the thicknesses of the collimators 328 are also different periodically, corresponding to the thicknesses of the separators 327. Specifically, the collimator 328a and the collimator 328c are designed to be relatively thin, and the collimator 328b and the collimator 328d are designed to be relatively thick. Namely, the relatively thin collimator 328 is disposed to correspond to the relatively thin separator 327, and the relatively thick collimator 328 is disposed to correspond to the relatively thick separator 327. Functions and advantages of these elements having different thicknesses will be described in detail in description of image acquiring processing by the X-ray CT device 100 as described later.

<Outline of Image Acquiring Processing>

Figure 3:
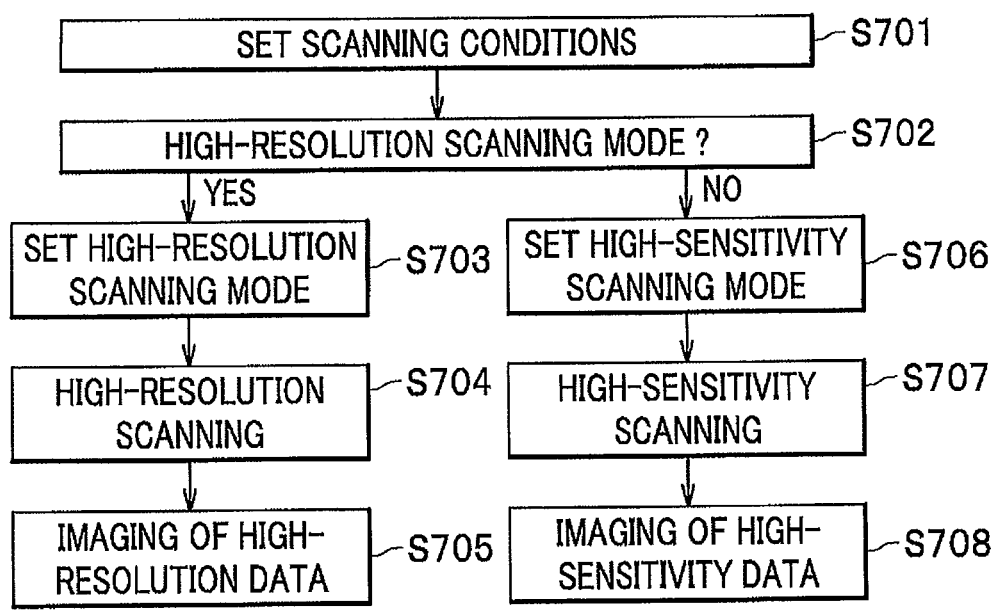
FIG. 3 is a flowchart showing an outline of image acquiring processing by the X-ray CT device.

Next, description is given of an outline of the image acquiring processing by the X-ray CT device 100. FIG. 3 is a flowchart showing an outline of the image acquiring processing by the X-ray CT device 100.

In the flowchart in FIG. 3, the X-ray CT device 100 first accepts setting of scanning conditions by an operator (step S701).

In the setting of scanning conditions, the X-ray CT device 100 displays entry screen of scanning conditions, by means of the scanning conditions input unit 210, on the monitor 213 or another monitor that does not constitute the X-ray CT device 100. The operator, looking at the entry screen, operates the mouse 212 and the keyboard 211 that constitute the scanning conditions input unit 210, or a touch panel sensor provided on the monitor 213, to thereby set a tube current and a tube voltage of the X-ray tube 311, a scanning range of the patient 500 and the like. Note that it is also possible to store scanning conditions beforehand and to read and use the stored information at the time of image acquisition. In this case, the operator does not have to input scanning conditions at every time of image acquisition.

Next, the X-ray CT device 100 judges based on the setting carried out in step S701, whether or not the scanning mode is a high-resolution scanning mode (step S702). Here, the X-ray CT device 100 has two scanning modes. One is a "high-resolution scanning mode" and another is a "high-sensitivity scanning mode". As to based on which mode this scanning is to be carried out, the X-ray CT device 100 may make a judgment based on the setting carried out in step S701, or the operator may input an arbitrary mode in step S701.

When the scanning mode is a high-resolution scanning mode (step S702, YES), the X-ray CT device 100 sets the high-resolution scanning mode (step S703). More specifically, the X-ray CT device 100 carries out setting to the DAS 411 (see FIG. 1) to independently treat signals detected by the respective detection elements when storing data. Namely, data size in the channel direction becomes the number of detection elements (e.g., 1000).

Then, the X-ray CT device 100 carries out high-resolution scanning (step S704). When the operator instructs the start of scanning, the X-ray CT device 100 carries out the scanning under the conditions of the scanning range, the tube voltage and the tube current which are set by the operator in the scanning conditions input unit 210 in step S701.

Concretely, the operator places the patient 500 (see FIG. 1, the same shall apply hereafter) on the patient-carrying table 501. The integrated controller 345 controls the table controller 343 to have the patient-carrying table 501 move in the direction perpendicular to the rotating plate 332 and to stop the movement at the time at which a scanning position on the rotating plate 332 and a scanning position specified in step S701 coincide with each other. By this control, placement of the patient 500 is completed.

Moreover, at the same timing, the integrated controller 345 controls the gantry controller 342 to have the rotary drive mechanism (not shown) of the rotating plate 332 operate and to start rotation of the rotating plate 332. When the rotation of the rotating plate 332 is brought into a constant-speed state and the placement of the patient 500 is finished, the integrated controller 345 instructs the X-ray controller 341 on the X-irradiation timing of the X-ray tube 311 and instructs the detector controller 344 on the scanning timing of the X-ray detector 321. Then, the X-ray CT device 100 starts the scanning.

The X-ray CT device 100 repeats these processings to image the entire scanning range. Note that although in the above description the scanning is carried out by repeating the movement and stop of the patient-carrying table 501, scanning may be carried out while moving the patient-carrying table 501, as in a publicly known helical scanning method.

Then, the X-ray CT device 100 carries out imaging of the data (high-resolution data) stored with the scanning in step S704 (step S705), and finishes the processings according to the present flowchart.

When the scanning mode is set to the high-resolution scanning mode, the X-ray detector 321 independently treat all of the signals of the scintillators 325a to 325d shown in FIGS. 2A and 2B, respectively, as set in step S703. Namely, the signals of the photodiodes 326a to 326d are, as separate data, converted through the DAS 411 into digital signals, which are temporarily stored in the HDD device 423.

When carrying out high-resolution scanning, since the signals from all of the detection elements are independently treated, respectively as described above, the high-resolution scanning has excellent resolution. On the other hand, there are parts using a thin member (relatively thin member) as compared to the normal, such as the separator 327a and the collimator 328a, and parts using a member of normal thickness (relatively thick member) such as the separator 327b and the collimator 328b. Accordingly, when carrying out imaging of the high-resolution data (step S705 in FIG. 3), it is necessary to carryout crosstalk correction, position correction and scattered radiation correction to thereby suppress influence by crosstalk, influence by scattered radiation, and a change in position.

Figure 4:
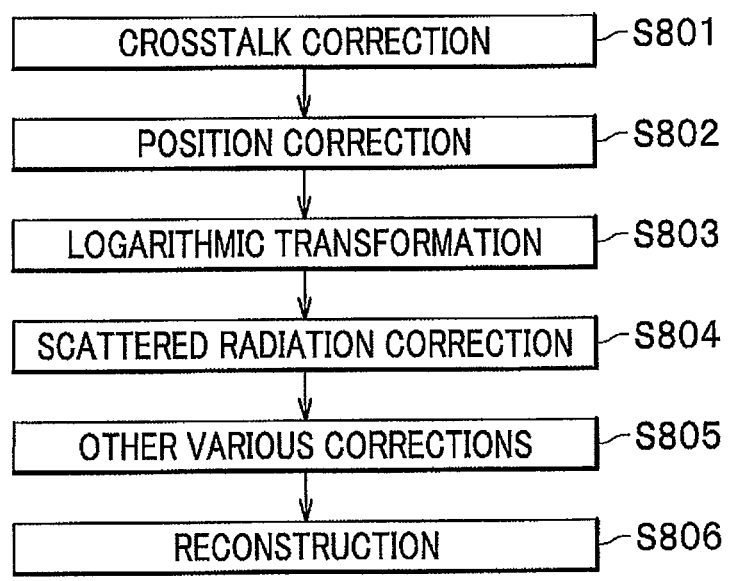
FIG. 4 is a flowchart showing detailed steps of imaging processing of high-resolution data.

FIG. 4 is a flowchart showing detailed steps of the imaging processing of the high-resolution data (step S705 in FIG. 3). Calculation in the imaging processing is all carried out by means of the central processing unit 421, the memory 422 and the HDD device 423 which are provided in the data processing unit 420 illustrated in FIG. 1.

In the flowchart in FIG. 4, the X-ray CT device 100 first carries out crosstalk correction for the high-resolution data acquired in step S703 in FIG. 3 (step S801).

The data acquired by the X-ray detector 321 of the X-ray CT device 100 includes parts which are large in the amount of crosstalk, and parts which are small in the amount of crosstalk. Since the amount of crosstalk is substantially dependent on the thickness of the separator, respective amounts of crosstalk in the separators 327a, 327c in FIGS. 2A and 2B become substantially the same value, and respective amounts of crosstalk in the separators 327b, 327d also become substantially the same. On the other hand, the amount of crosstalk in the separators 327a, 327c and the amount of crosstalk in the separators 327b, 327d differ greatly from each other.

For this reason, the crosstalk correction is carried out with a total of two correction values of the amount of crosstalk correction for the separators 327a, 327c (in addition, other separators having the same thickness as that of the separator 327a), and the amount of crosstalk correction for the separators 327b, 327d (in addition, other separators having the same thickness as that of the separator 327b). This makes it possible to reduce the number of correction data.

Note that when the X-ray detector 321 has a module structure, it is necessary to consider the amount of crosstalk at ends of the module in conjunction with the above because crosstalk correction values differ from each other at the ends of the module. Moreover, when the X-ray detector 321 is a semiconductor detector, crosstalk by electrons in the detector may not be generated and only crosstalk by X-rays may be generated, depending on how to make the detector. In this case, it is only necessary to carry out only crosstalk correction for X-rays without carrying out crosstalk correction for electrons.

Next, the X-ray CT device 100 carries out position correction for the high-resolution data (step S802). Although the detection elements (scintillators 325, photodiodes 326) of the X-ray detector 321 are not arrayed at equal pitches, the reconstruction processing requires equal-pitch data. To this end, the equal-pitch data is prepared in the position correction. The concrete way is, for example, to use data at two points which are closest to the position of required data and to calculate equal-pitch data by interpolation processing. Note that in the case of not requiring equal-pitch data, or in the case of detected data being approximately regarded as equal-pitch data, such as the case of employing successive reconstruction method, the processing of step S802 does not have to be carried out.

Subsequently, the X-ray CT device 100 carries out logarithmic transformation for the high-resolution data (step S803). Signals of X-rays and light generally decay exponentially in the process of transmission and scattering. To cope with this, the X-ray CT device 100 carries out the logarithmic transformation for the data. The logarithmic transformation for the data leads to an advantage in calculation that it is possible to treat the amount of calculation of product as the amount of calculation of sum.

Next, the X-ray CT device 100 carries out scattered radiation correction for the high-resolution data (step S804). As shown in FIGS. 2A and 2B, the thicknesses of the collimators 328 are different periodically. In particular, in the thin collimator 328, there occurs direction dependency with respect to a direction along which scattered radiation enters. It is scattered radiation correction that corrects the direction dependency. The scattered radiation correction is carried out by utilizing the properties that the rate of change in the amount of scattered radiation is very gradual and direction dependency is low.

Subsequently, the X-ray CT device 100 carries out the other various corrections (step S805). These corrections are carried out when there are matters and/or phenomena for which you had better carry out correction, other than the corrections shown in steps S801 to S804. Therefore, the processing in step S805 may not be carried out. Moreover, the order of steps S801 to S805 may be changed as needed. Furthermore, various corrections in step S805 may be carried out more than once. For example, various corrections may be carried out in twice, after the position correction (step S802) and after the scattered radiation correction (step S804).

Then, the X-ray CT device 100 carries out reconstruction of the high-resolution data (step S806), and finishes the processings according to the present flowchart. Note that post-reconstruction image acquired in step S806 is stored in the HDD device 423 (see FIG. 1). The stored image is displayed on the image display monitor 441 (see FIG. 1) according to instruction from the operator or automatically, and the operator uses the image to make a diagnosis or the like.

Referring back to the description of FIG. 3, in step S702, when the scanning mode is a high-sensitivity scanning mode (step S702, NO), the X-ray CT device 100 sets the high-sensitivity scanning mode (step S706). In the high-sensitivity scanning mode, of the scintillators 325*a* to 325*d*, an output signal from the scintillator 325*a* and an output signal from the scintillator 325*b* are treated as an output signal from a single scintillator 325. Moreover, an output signal from the scintillator 325*c* and an output signal from the scintillator 325*d* are treated as an output signal from a single scintillator 325. Namely, two scintillators 325 adjoining to a relatively thin separator 327 are treated as the single scintillator 325.

More specifically, an output signal of the photodiode 326*a* and an output signal of the photodiode 326*b* are added in the DAS 411 and then stored in the HDD device 423. Moreover, an output signal of the photodiode 326*c* and an output signal of the photodiode 326*d* are added in the DAS 411 and then stored in the HDD device 423. AS for the addition method, for example, a publicly known technique such as described in the above Patent Literature 2 is employed. In the high-sensitivity scanning mode, data size in the channel direction becomes half the number of detection elements (500 in this case).

Then, the X-ray CT device 100 carries out high-sensitivity scanning (step S707). Concrete scanning method is the same as that in step S704. In the X-ray CT device 100, signals acquired by the X-ray detector 321 are added in the DAS 411 and then stored in the HDD device 423. At this time, the DAS 411 adds signals of the detection elements which sandwiches the separator 327*a*, 327*c* having a relatively thin thickness therebetween, as described above. This is because the thickness of the separator 327*a*, 327*c* is thin and reduction in sensitivity in this position is small as compared to the separator 327*b*, 327*d*.

Therefore, when carrying out high-sensitivity scanning, the number of counts per detection element becomes increased, compared with the case where all of the separators 327 have the thickness of the relatively thick separator 327*b*, 327*d*. Moreover, since the effects by the separators 327*b*, 327*d* and the collimators 328*b*, 328*d* are kept, it is possible to reduce influences by crosstalk and/or scattered radiation. When the influences by crosstalk and/or scattered radiation can be sufficiently removed, there is also a possibility that a sufficient image can be acquired without having to carry out crosstalk correction and/or scattered radiation correction. Namely, high-sensitivity scanning mode has resistance to deterioration of images.

Then, the X-ray CT device 100 carries out imaging of the data (high-sensitivity data) stored with the scanning in step S707 (step S708), and finishes the processings according to the present flowchart.

Figure 5:
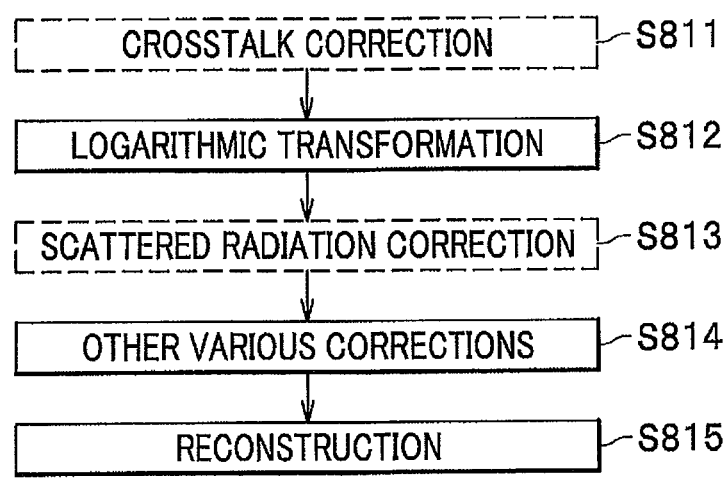
FIG. 5 is a flowchart showing detailed steps of imaging processing of high-sensitivity data.

FIG. 5 is a flowchart showing detailed steps of the imaging processing of the high-sensitivity data (step S708 in FIG. 3). Calculation in the steps of imaging is all carried out by means of the central processing unit 421, the memory 422 and the HDD device 423 which are provided in the data processing unit 420 illustrated in FIG. 1.

In the flowchart in FIG. 5, the X-ray CT device 100 first carries out crosstalk correction for the high-sensitivity data acquired in step S707 in FIG. 3 (step S811).

Specifically, in the case of high-sensitivity data, data of the detectors (the photodiode 326*a* and the photodiode 326*b*) which are located right and left of the separator 327*a* in FIG. 2A are added. Moreover, data of the detectors (the photodiode 326*c* and the photodiode 326*d*) which are located right and left of the separator 327*c* are added. Accordingly, no correction is needed for crosstalk between the photodiode 326*a* and the photodiode 326*b*, and between the photodiode 326*c* and the photodiode 326*d*. Namely, only crosstalk correction in the separators 327*b*, 327*d* is carried out.

Since the data of the photodiode 326*a* and the photodiode 326*b*, and the data of the photodiode 326*c* and the photodiode 326*d*, are added respectively, a different value from the value of crosstalk correction (step S801 in FIG. 4) for the high-resolution data is used as the amount of crosstalk. Note that when the X-ray detector 321 has a module structure, it is necessary to consider the amount of crosstalk at ends of the module in conjunction with the above because crosstalk correction values differ from each other at the ends of the module. Also, when the X-ray detector 321 is a semiconductor detector, crosstalk by electrons in the detector may not be generated and only crosstalk by X-rays may be generated, depending on how to make the detector. In this case, it is only necessary to carryout only crosstalk correction for X-rays without carrying out crosstalk correction for electrons. Moreover, when the separator 327 is sufficiently thick, crosstalk is hardly generated. In this case, crosstalk correction does not have to be carried out.

Subsequently, the X-ray CT device 100 carries out logarithmic transformation for the high-sensitivity data (step S812). The reason for carrying out logarithmic transformation is the same as that for step S803 in FIG. 4.

Note that in the high-sensitivity scanning mode, since the same data as that obtained when the centers of the respective detection elements to be added are located at equal spaces is acquired, the position correction shown in step S802 in FIG. 4 is basically unnecessary. However, when the detectors are not arranged at equal pitches for reasons other than the thickness of the separator 327, the position correction may also be carried out.

Next, the X-ray CT device 100 carries out scattered radiation correction for the high-resolution data (step S813). Also with respect to the scattered radiation correction, in the same manner as the crosstalk correction, the data of the photodiode 326*a* and the photodiode 326*b*, and the data of the photodiode 326*c* and the photodiode 326*d*, are added respectively, and accordingly, as for the influence by scattered radiation, it is only necessary to take into account only the portions at which the thick collimators 328 are used. Moreover, when the collimators 328 sufficiently remove scattered radiation, the scattered radiation correction does not have to be carried out, and only when required, the scattered radiation correction is carried out.

Subsequently, the X-ray CT device 100 carries out various corrections which are other corrections (step S814). These corrections are carried out when there are matters and/or phenomena for which you had better carry out correction, other than the corrections shown in steps S811 to S813. Therefore, the processing in step S814 may not be carried out. Moreover, the order of steps S811 to S814 may be changed as needed.

Then, the X-ray CT device 100 carries out reconstruction of the high-resolution data (step S815), and finishes the processings according to the present flowchart. Note that post-reconstruction image acquired in step S815 is stored in the HDD device 423 (see FIG. 1). The stored image is displayed on the image display monitor 441 (see FIG. 1) according to instruction from the operator or automatically, and the operator uses the image to make a diagnosis or the like.

As described above, the X-ray CT device 100 according to the first embodiment makes it possible to have a structure adapted to suppress reduction in sensitivity when acquiring high-resolution data, as much as possible, and to suppress reduction in sensitivity when carrying out the high-resolution scanning (high-resolution scanning mode).

Specifically, as shown in FIGS. 2A and 2B, the X-ray detector 321 in the X-ray CT device 100 according to the first embodiment has the structure in which the relatively thin separators 327 (327a, 327c) are periodically arranged, thereby making it possible to reduce an area of blind parts (separators 327) other than the detection elements (scintillators 325, photodiodes 326) to arrange as many as possible of the detection elements. Accordingly, it becomes possible to enhance sensitivity of the X-ray detector 321, compared with the conventional X-ray CT device (for example, see Patent Literature 2) in which blind parts having a uniform width are arranged at equal spaces.

Moreover, the relatively thin collimators 328 (328a, 328c) are disposed on the relatively thin separators 327 (327a, 327c). Accordingly, it is possible to enhance anti-scatter capability and to suppress deterioration of image quality, compared with the conventional X-ray CT device (for example, see Patent Literature 2) in which a plurality of detection elements are arranged for one X-ray transmission part of an X-ray shielding member.

Note that when carrying out the high-sensitivity scanning (high-sensitivity scanning mode) in the X-ray CT device 100 according to the first embodiment, due to that the relatively thin collimators 328 (328a, 328c) are disposed, compared with the conventional X-ray CT device (for example, see Patent Literature 2), the sensitivity is reduced as compared to the case where the thin collimators 328 (328a, 328c) are not disposed. However, as described above, the X-ray CT device 100 reduces the blind parts to arrange as many as possible of the detection elements to thereby enhance the sensitivity of the X-ray detector 321, and thus can appropriately carry out the high-sensitivity scanning.

Moreover, materials of the thick collimator 328 (e.g., the collimators 328b, 328d in FIGS. 2A and 2B) and the thin collimator 328 (e.g., the collimators 328a, 328c in FIGS. 2A and 2B) may be changed. Specifically, for the thick collimator 328, inexpensive material (e.g., lead) may be used, and for the thin collimator 328, material which is expensive but dense with high X-ray blocking capability (e.g., tungsten) may be used. In this case, the thin collimator 328 can enhance anti-scatter capability because of its high X-ray blocking capability and suppress deterioration of image quality, and the thick collimator 328 uses inexpensive material to make it possible to suppress raw material cost.

<Relationship Between the Width of the Separator 327 and the Thickness of the Collimator 328>

Figure 6:
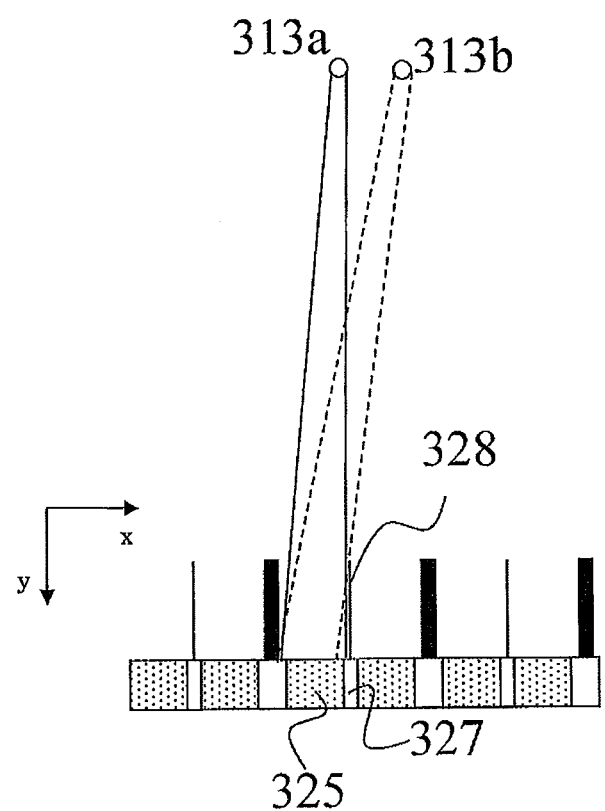
FIG. 6 is an explanatory view schematically showing a change in the amount of incident X-ray by movement of a position of X-ray focal spot.

Here, description is given of restriction of the thickness of the collimator 328 due to movement of the position of X-ray focal spot. FIG. 6 is an explanatory view schematically showing a change in the amount of incident X-ray by movement of the position of X-ray focal spot.

In the X-ray CT device 100, the position of X-ray focal spot of the X-ray tube 311 (see FIG. 1) may move in connection with thermal displacement or the like. When the position of X-ray focal spot moves, a portion of X-ray is blocked by influence of the collimator 328 and the amount of X-ray directly incident on the scintillator 325 (detection element) is changed, thereby making data inaccurate. For example, when the X-ray focal spot is at a position 313a in FIG. 6, the amount of X-ray directly incident on the scintillator 325 (detection element) becomes as shown by solid lines. Moreover, when the X-ray focal spot is at a position 313b, the amount of X-ray directly incident on the scintillator 325 (detection element) becomes as shown by broken lines.

Thus, when the X-ray focal spot is at the position 313b, the incident X-ray is limited by influence of the collimator 328, thereby making an output signal of the scintillator 325 (detection element) greatly change. Namely, the sensitivity of the detection elements in the X-ray detector 321 is changed due to thermal displacement.

Figure 7:
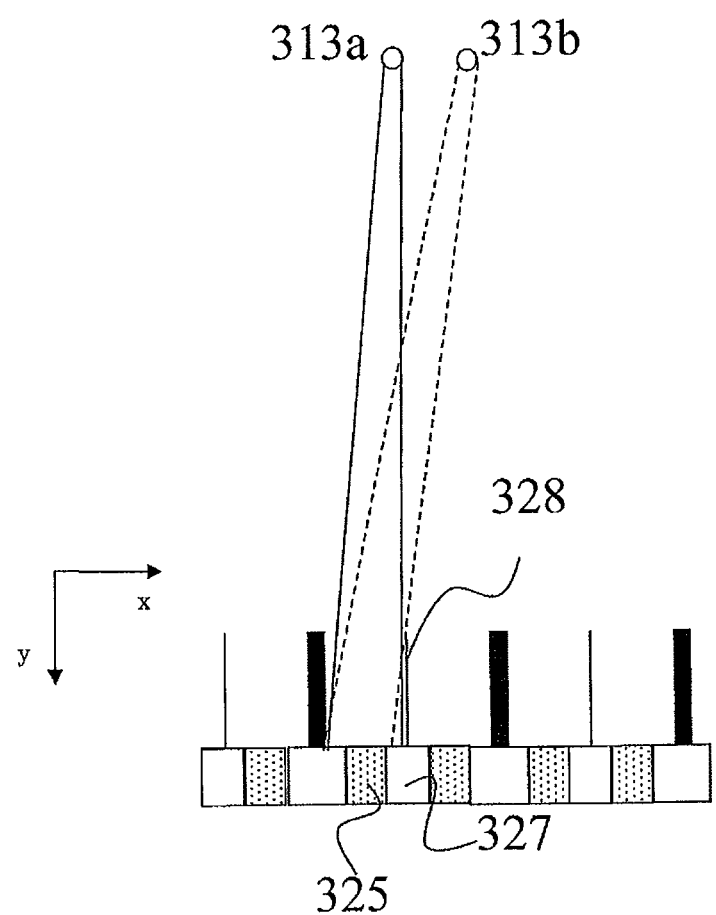
FIG. 7 is a schematic view enlarging part of the X-ray detector in consideration of movement of a position of X-ray focal spot when viewing the X-ray detector in a slice direction.

To cope with this, the designing is made so that a change in the X-ray blocking area generated by movement of the position of X-ray focal spot (sensitivity change due to thermal displacement) does not affect the scintillator 325 (detection element). FIG. 7 is a schematic view enlarging part of the X-ray detector in consideration of movement of the position of X-ray focal spot when viewing the X-ray detector in the slice direction.

As shown in FIG. 7, in order that the sensitivity is not changed even when the position of X-ray focal spot moves from the position 313a to the position 313b, the designing is made so that shadow by the collimator 328 falls within the separator 327.

On the other hand, it is preferable to make the collimator 328 thick for anti-scatter. Therefore, for balancing anti-scatter capability with suppression of a sensitivity change due to thermal displacement, it is preferable to make the collimator 328 as thick as possible for use in the range in which the suppression of a sensitivity change due to thermal displacement is possible.

Here, the collimator 328 is generally designed to face toward the center direction in the movement of the X-ray focal spot. Moreover, in FIGS. 6 and 7, the distance between the positions 313a, 313b of X-ray focal spot and the scintillator 325 (detection element) is shortly depicted because of space limitations. As described above, however, in the X-ray CT device 100 according to the first embodiment, the distance between the X-ray originating point (X-ray focal spot) of the X-ray tube 311 and the X-ray input plane of the X-ray detector 321 is, for example, 1000 mm, and the width in the channel direction of each scintillator 325 is, for example, 1 mm.

Figure 8:
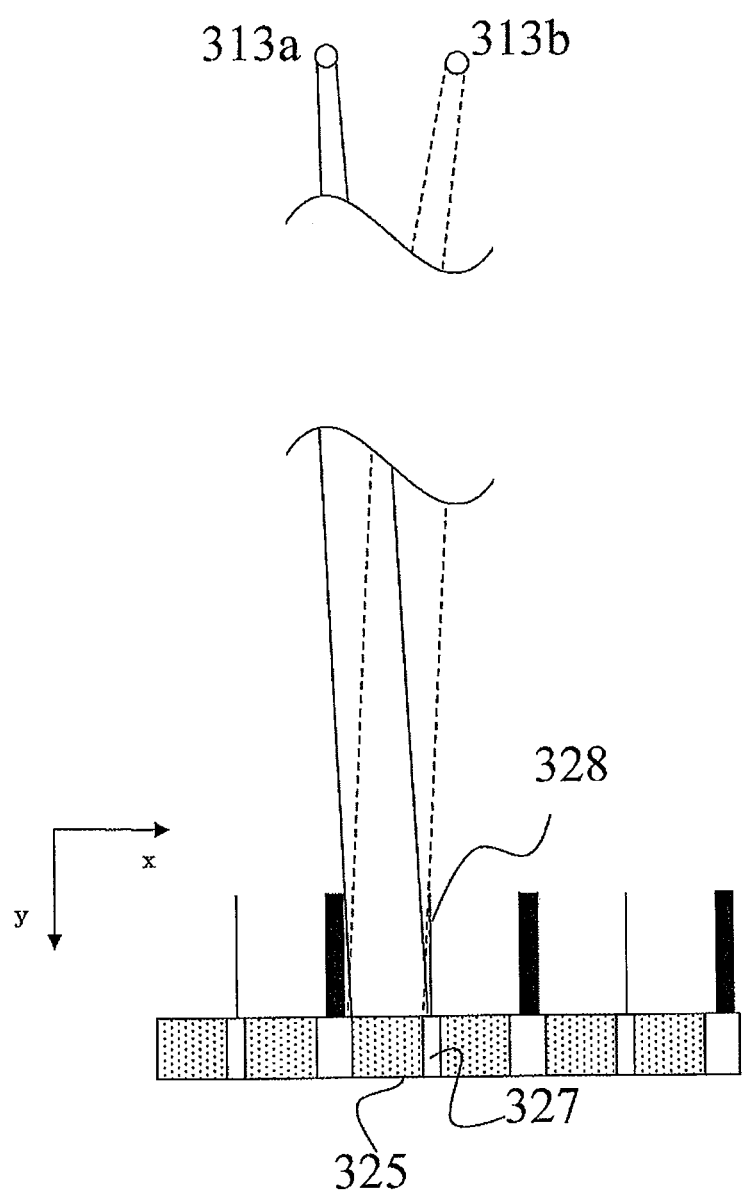
FIG. 8 is an explanatory view schematically showing a change in the amount of incident X-ray by movement of a position of X-ray focal spot, which is depicted in consideration of relationship of lengths.

FIG. 8 is an explanatory view schematically showing a change in the amount of incident X-ray by movement of the position of X-ray focal spot, which is depicted in consideration of relationship of lengths. When the center of the positions 313a, 313b of X-ray focal spot and the center position of the scintillator 325 (detection element) are aligned with each other, as shown in FIG. 8, for any of the thick collimator 328 (e.g., the collimators 328b, 328d in FIGS. 2A and 2B) and the thin collimator 328 (e.g., the collimators 328a, 328c in FIGS. 2A and 2B), the distance of the area which is the shadow by the collimator 328 (distance from the end of the collimator 328) becomes approximately the same, because the distance between the X-ray originating point (X-ray focal spot) of the X-ray tube 311 and the X-ray input plane of the X-ray detector 321 is sufficiently long.

Therefore, it is the condition under which the permissible amount of thermal displacement for the X-ray focal spot is the same and the anti-scatter capability becomes the highest in the thick collimator 328 and the thin collimator 328, that a difference between the thickness of the thick separator 327 and the thickness of the thick collimator 328, and a difference between the thickness of the thin separator 327 and the thickness of the thin collimator 328, become approximately the same.

In other words, it is the condition under which the permissible amount of thermal displacement for the X-ray focal spot is the same and the anti-scatter capability becomes the highest in the separator 327 having any of the thicknesses, that a difference between the thickness $W_{327}$ of the separator 327 and the thickness $W_{328}$ of the collimator 328 corresponding to the separator 327 becomes approximately a predetermined value M (namely, $W_{327}-W_{328} \approx M$).

Note that it is difficult to set the thickness of the separator 327 and the thickness of the collimator 328 to be the values as designed, and in addition, it is actually necessary to take process errors and individual variability by thermal displacement into consideration. Considering a margin of about 10% with respect to the consideration, when manufacturing is carried out under the condition that the difference between the thickness of the thick separator 327 and the thickness of the thick collimator 328, and the difference between the thickness of the thin separator 327 and the thickness of the thin collimator 328, are less than 10%, it becomes possible to balance the permissible amount of thermal displacement with the anti-scatter capability.

In other words, in any of the separators 327, when the difference between the thickness $W_{327}$ of the separator 327 and the thickness $W_{328}$ of the collimator 328 corresponding to the separator 327 satisfies the relation of expression (1), it becomes possible to balance the permissible amount of thermal displacement with the anti-scatter capability. Note that M is a predetermined value which is determined by the distance between the X-ray originating point (X-ray focal spot) of the X-ray tube 311 and the X-ray input plane of the X-ray detector 321, the height of the collimator 328, the width of the detection element (scintillator 325), and the like.

[Mathematical formula 1]

$$0.9 \times M \leq W_{327}-W_{328} \leq 1.1 \times M \quad (1)$$

By satisfying the relation of expression (1), it becomes possible to design an X-ray detector with a size capable of most reducing scattered radiation because the permissible amount of thermal displacement becomes a kept state and the anti-scatter capability becomes the highest in the thin collimator 328.

Modified Example of the First Embodiment

Reinforcement of the Collimator 328

Figure 9A:
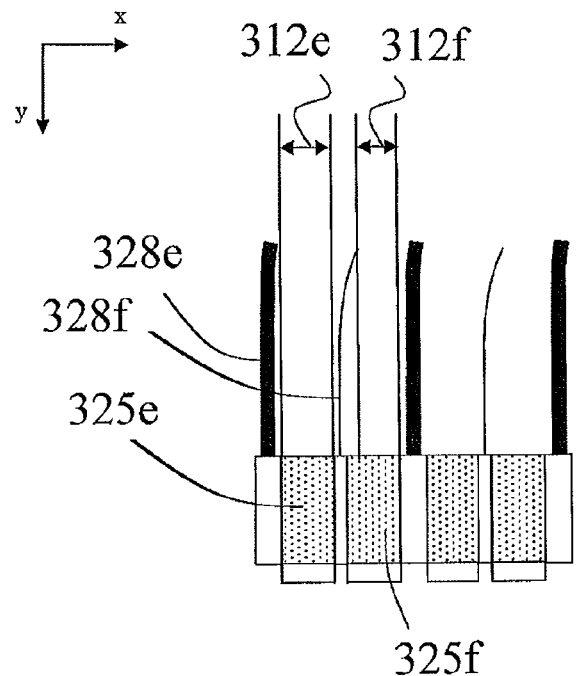

Hereinafter, a modified example of the X-ray CT device 100 is described. FIG. 9A is an explanatory view schematically showing the X-ray detector 321 which is in rotation. In the X-ray CT device 100, the X-ray detector 321 rotates within the gantry 330 while the thick collimator 328 and the thin collimator 328 receive different stresses. Due to the difference of stresses, deflections of the respective collimators 328 also differ from each other.

For example, as shown in FIG. 9A, the thin collimator 328f may deflect greatly as compared to the thick collimator 328e. In this case, widths of direct radiation which can enter the scintillator 325e and the scintillator 325f are a width 312e and a width 312f, respectively, and thus the amount of radiation incident on the scintillator 325 is changed.

Figure 9B:
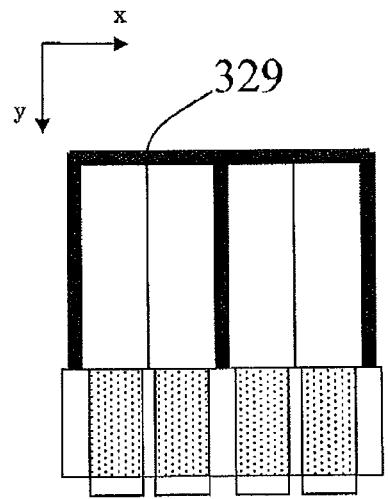
Figure 9C:
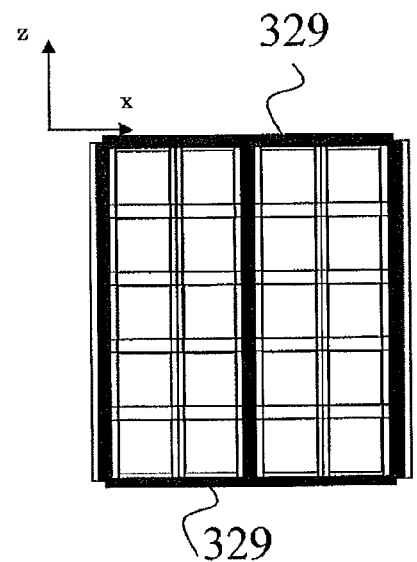

Therefore, in order to uniform deflections of the respective collimators 328, as shown in FIGS. 9B and 9C, the collimator 328 may be fixed with a collimator reinforcing member 329 connected to the end portion thereof. FIG. 9B is a view when viewing the X-ray detector 321 according to a first modified example in the z-direction (the slice direction, the body-axis direction of the patient 500), and FIG. 9C is a view when viewing the X-ray detector 321 according to the first modified example in the y-direction (the X-ray irradiation direction).

Note that in FIG. 9C, although the collimator 328 is fixed at both ends (end portions in the z-direction) with the collimator reinforcing members 329, a further collimator reinforcing member 329 may be added in between when deflection in the central portion by high speed rotation differs from the other portion.

Moreover, although not shown, there is also an approach to suppress deformation by inserting between the collimators 328 a deformation-preventing member which is easy to transmit X-rays therethrough. Thus, by reinforcing the collimators 328, the X-ray CT device 100 uniforms influences by deformations of the collimators 328, thereby making it possible to remove uneven sensitivity and to improve image quality.

<Array in Two Directions>

Figure 10:
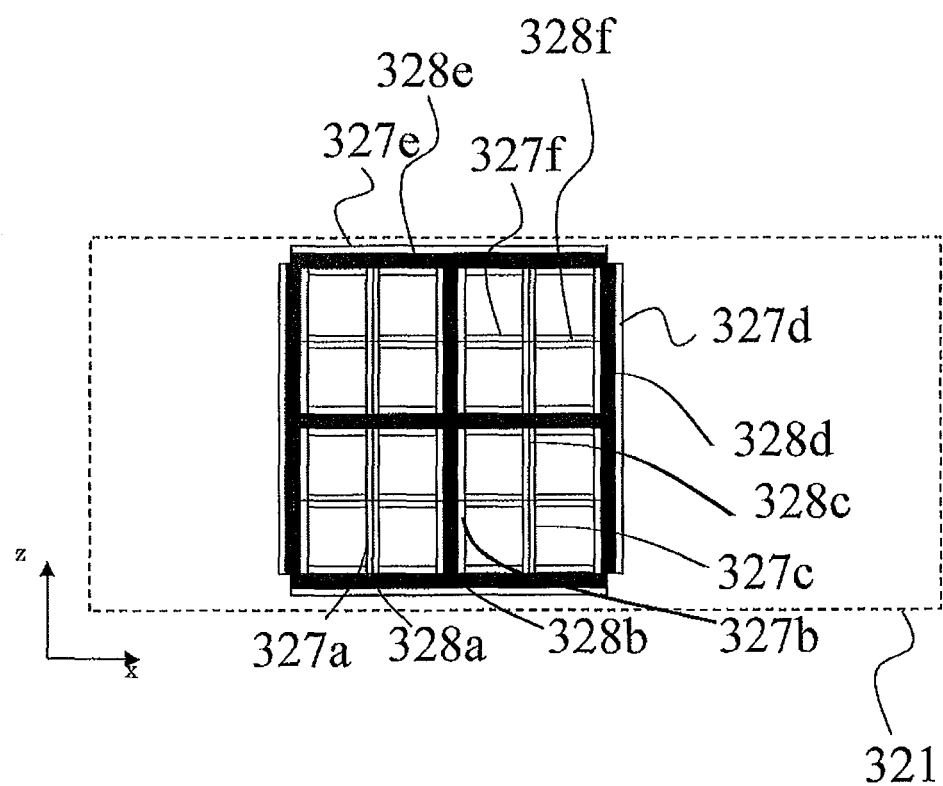
FIG. 10 is an enlarged schematic view enlarging part of an X-ray detector according to a second modified example when viewing the X-ray detector in an X-ray irradiation direction.

Although the description has been heretofore given of the structure in which the collimators 328 are arranged in one direction and the respective thicknesses of the separators 327 and the collimators 328 are periodically changed in the one direction, the periodic structure may be developed two-dimensionally in two directions. FIG. 10 is an enlarged schematic view enlarging part of an X-ray detector according to a second modified example when viewing the X-ray detector in the X-ray irradiation direction.

In FIG. 10, the X-ray detector 321 includes, in addition to the separators 327a to 327d and the collimators 328a to 328d arrayed in the x-direction, separators 327e, 327f and collimators 328e, 328f arrayed also in the z-direction. Of these separators, the separator 327e becomes relatively thick and the separator 327f becomes relatively thin. Moreover, corresponding to this, the collimator 328e becomes relatively thick and the collimator 328f becomes relatively thin.

By adopting such configuration, the X-ray CT device 100 makes it possible to carry out a switching between high-resolution scanning mode and high-sensitivity scanning mode in two directions, and by combining those modes together, to carry out scanning according to more flexible settings (resolution and sensitivity). Moreover, by adopting such grid structure in the X-ray detector 321, it is possible to suppress influence by the deflection associated with rotation, and as described with respect to the above collimator reinforcement, to reduce uneven sensitivity to thereby improve image quality of reconstructed images.

Second Embodiment

Next, description is given of the X-ray CT device 100 according to a second embodiment.

The X-ray CT device 100 according to the first embodiment and the X-ray CT device 100 according to the second embodiment are the same except for a difference in the configuration of the X-ray detector 321, as to the other configuration (see FIG. 1) and the scanning processing (see FIG. 3 to FIG. 5), and thus description thereof is omitted.

In the X-ray CT device 100 according to the first embodiment, the heights of the collimators 328 in the X-ray detector 321 are all made equal as shown in FIG. 2A, and study has been made on the problem of sensitivity difference due to thermal displacement with reference to FIGS. 6 to 8. However, owing to process limitation or the like as to the thicknesses of the collimators 328 and the separators 327, it may be impossible to manufacture the device under the condition that the difference between the thickness of the thick separator 327 and the thickness of the thick collimator 328, and the difference between the thickness of the thin separator 327 and the thickness of the thin collimator 328, are equal to or less than 10% (namely, expression (1)).

Figure 11:
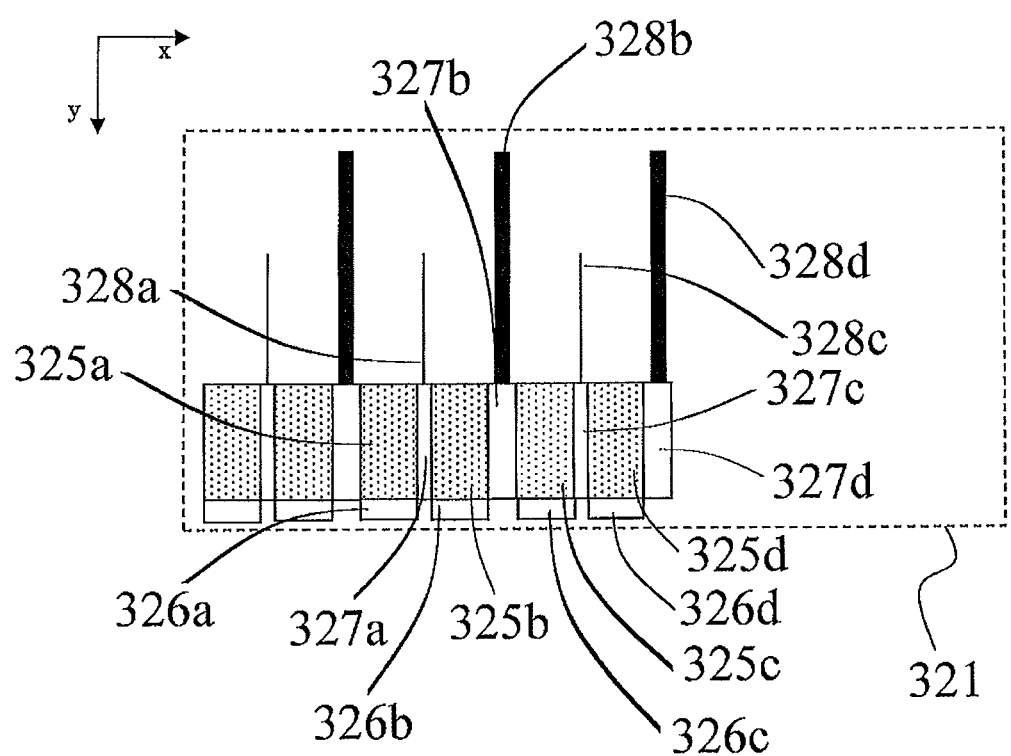
FIG. 11 is a schematic view enlarging part of an X-ray detector according to a second embodiment when viewing the X-ray detector in a slice direction.

To cope with this, the second embodiment makes the heights of the collimators 328 different periodically as shown in FIG. 11 to thereby suppress a change in the amount of incident X-ray (change in sensitivity) by movement of a position of the X-ray focal spot.

The X-ray detector 321 according to the second embodiment (see FIG. 11) makes lower the heights of the collimators 328a, 328c which are located on the thin separators 327, i.e., the separators 327a, 327c, compared with the X-ray detector 321 according to the first embodiment (see FIG. 2A). Consequently, it is possible to suppress a change in the amount of direct incident X-ray by influences of the collimators 328a, 328c and to expand an acceptable range of the movement in position of the X-ray focal spot 313. Moreover, instead of expanding the acceptable range of the movement in position of the X-ray focal spot 313, the thicknesses of the separators 327a, 327c may be made thinner.

Here, with respect to the heights of the thin collimators 328 (328a, 328c), consideration is made on the condition under which the collimators 328 are used with being made as thick as possible in the range in which suppression of the sensitivity change due to thermal displacement is possible.

Figure 12:
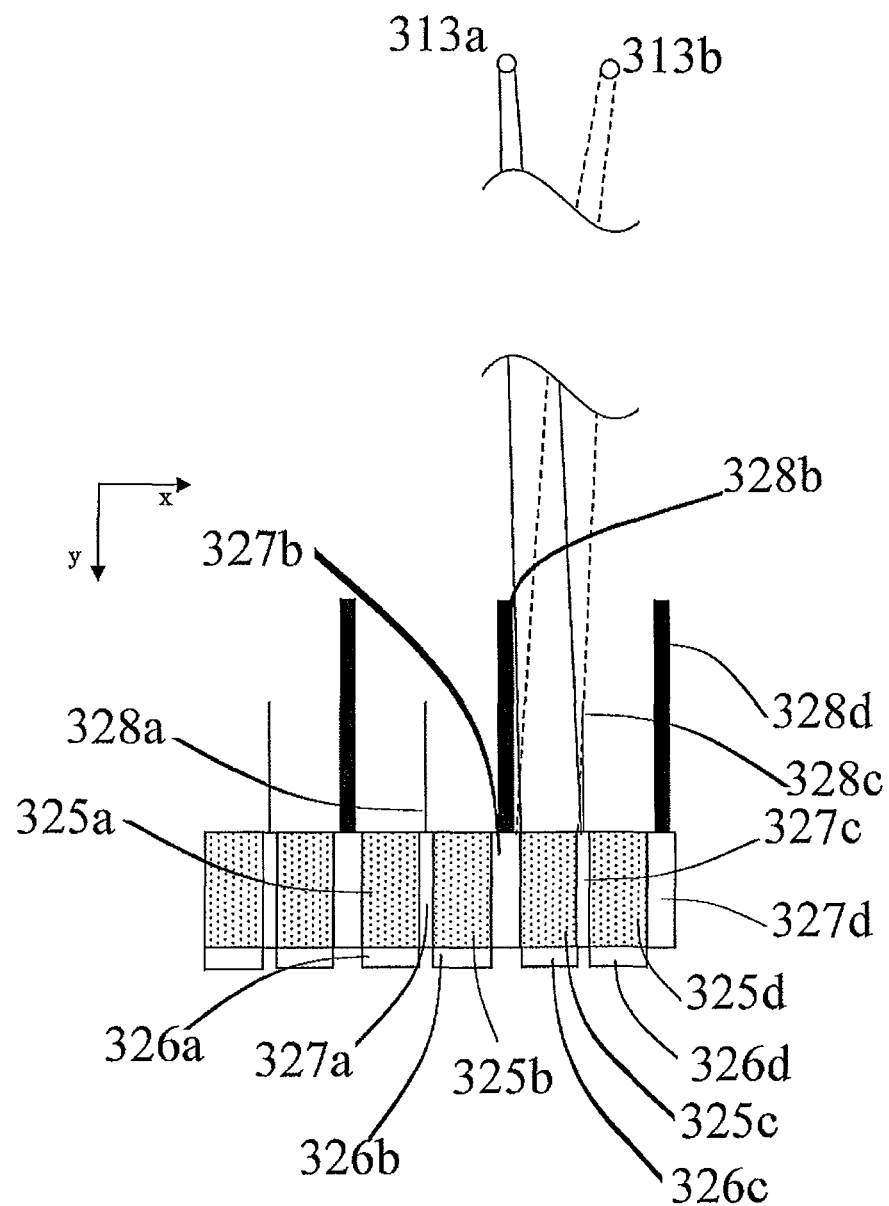
FIG. 12 is an explanatory view schematically showing a change in the amount of incident X-ray by movement of a position of X-ray focal spot.

As shown in FIG. 12, consideration is made on the case of irradiation between the collimator 328b and the collimator 328c. In order to make the thicknesses of the collimators 328 as thick as possible so that the sensitivity is not changed even if the collimators are moved due to thermal displacement, and anti-scatter capability is enhanced, it is preferable that for both of the thick separator 327b and the thin separator 327c, differences between the thicknesses of the separators 327 and the thicknesses of the collimators 328 are equal to a ratio of heights of the collimators 328, i.e., that the relation of expression (2) is satisfied, under approximation that the distance between the X-ray originating point (X-ray focal spot) of the X-ray tube 311 and the X-ray input plane of the X-ray detector 321 is sufficiently long as compared to the width in the channel direction of each scintillator 325, and that the angle of incidence is the same.

Note that in the expression (2), $W_{327L}$ is a thickness of the thick separator 327, $W_{328L}$ is a thickness of the thick collimator 328, $W_{327S}$ is a thickness of the thin separator 327, $W_{328S}$ is a thickness of the thin collimator 328, $H_{328L}$ is a height of the thick collimator 328, and $H_{328S}$ is a height of the thin collimator 328.

[Mathematical formula 2]

$$\frac{H_{328S}}{W_{327S} - W_{328S}} = \frac{H_{328L}}{W_{327L} - W_{328L}} \quad (2)$$

Taking process errors, individual variability by thermal displacement and a margin of about 10% into consideration in the same way as in the first embodiment, it is possible to balance the permissible amount of thermal displacement with the anti-scatter capability when the relation of expression (3) is satisfied. Note that in the expression (3), $W_{327L}$, is a thickness of the thick separator 327, $W_{328L}$ is a thickness of the thick collimator 328, $W_{327S}$ is a collimator 328, $H_{328L}$ is a height of the thick collimator 328, and $H_{328S}$ is a height of the thin collimator 328.

[Mathematical formula 3]

$$0.9 \times \frac{W_{327S} - W_{328S}}{W_{327L} - W_{328L}} \cdot H_{328L} \leq H_{328S} \leq 1.1 \times \frac{W_{327S} - W_{328S}}{W_{327L} - W_{328L}} \cdot H_{328S} \quad (3)$$

Figure 13:
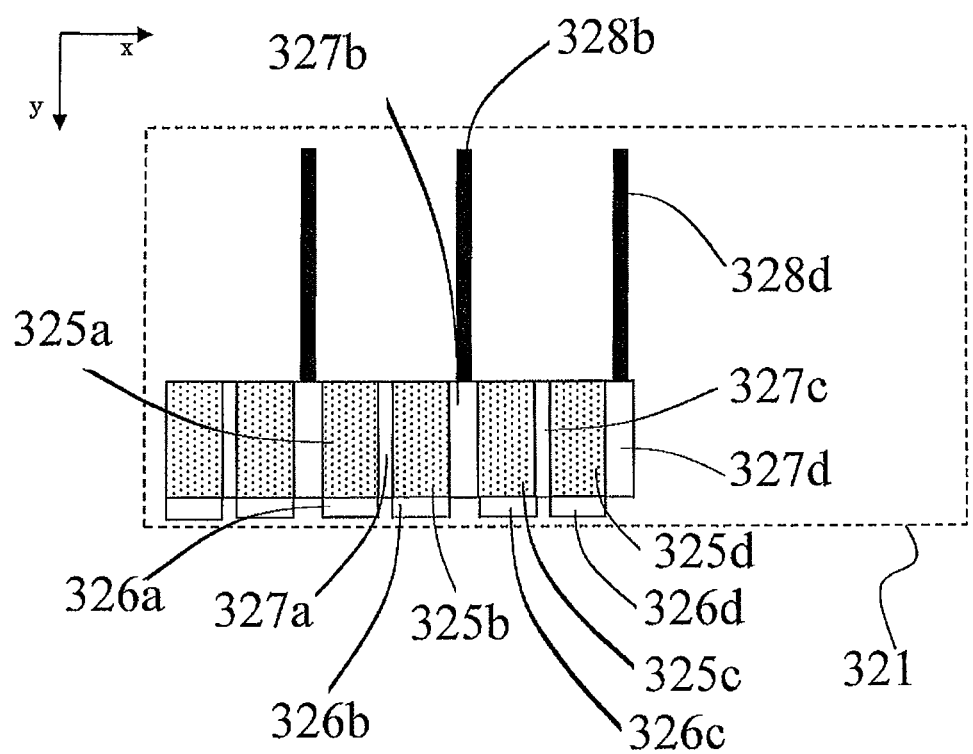
FIG. 13 is a schematic view enlarging part of an X-ray detector according to a modified example of the second embodiment when viewing the X-ray detector in a slice direction.

Moreover, as shown in FIG. 13, it is also possible to directly suppress a change in the amount of incident X-ray by not disposing some of the collimators 328 in the X-ray detector 321. In FIG. 13, the collimators 328 are not disposed on the relatively thin separators 327a, 327c. In this case, shadow by the collimators 328 is not formed on the thin separators 327a, 327c. Therefore, it becomes possible to do the design in consideration of only the heights of the collimators 328b, 328d on the thick separators 327b, 327d.

As described above, the X-ray CT device 100 according to the second embodiment makes it possible to reduce influence by the shadow due to the focal spot position dependency of the amount of incident X-ray and/or manufacturing errors and to suppress uneven sensitivity to thereby improve image quality of reconstructed images.

Third Embodiment

In the first embodiment and the second embodiment, the thicknesses of the separators 327 and the like are alternately changed. More specifically, in the first embodiment and the second embodiment, the thicknesses of the separators 327 and the like are changed with two pitches. The third embodiment differs from the first embodiment and the second embodiment, in the period with which the thicknesses of the separators 327 and the like are changed. This makes it possible to obtain an X-ray CT device 100 which can further improve the degree of freedom for sensitivity and resolution and can accommodate various examinations.

Figure 14A:
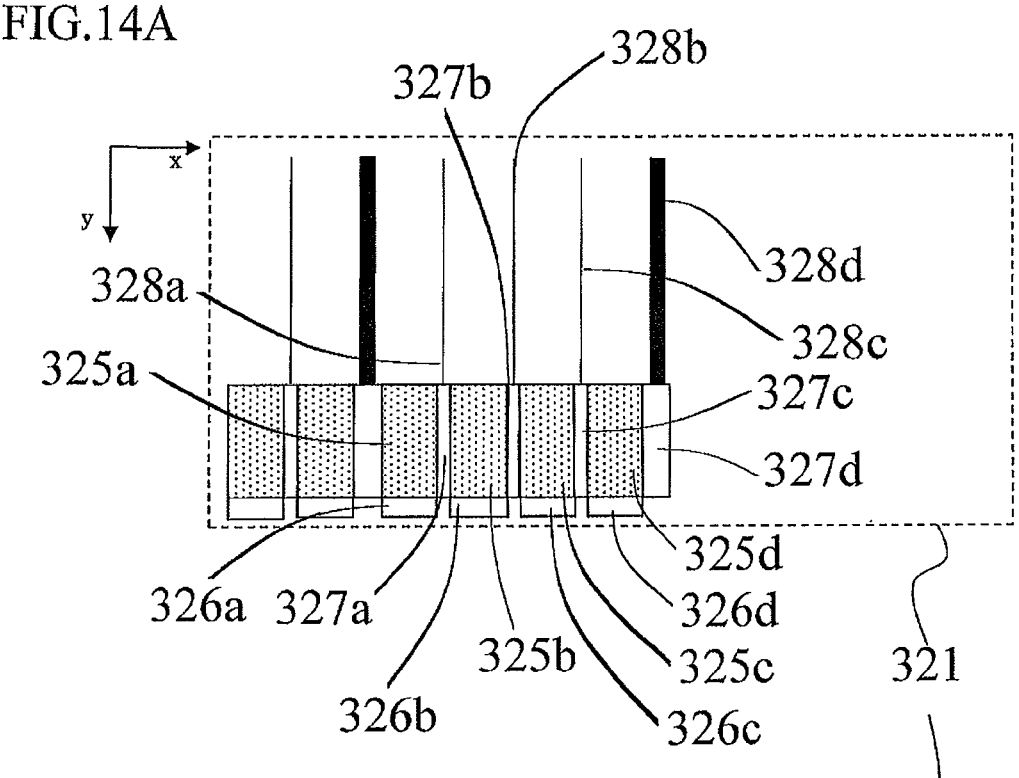
FIGS. 14A and 14B are schematic views enlarging part of an X-ray detector according to a third embodiment when viewing the X-ray detector in a slice direction.
Figure 14B:
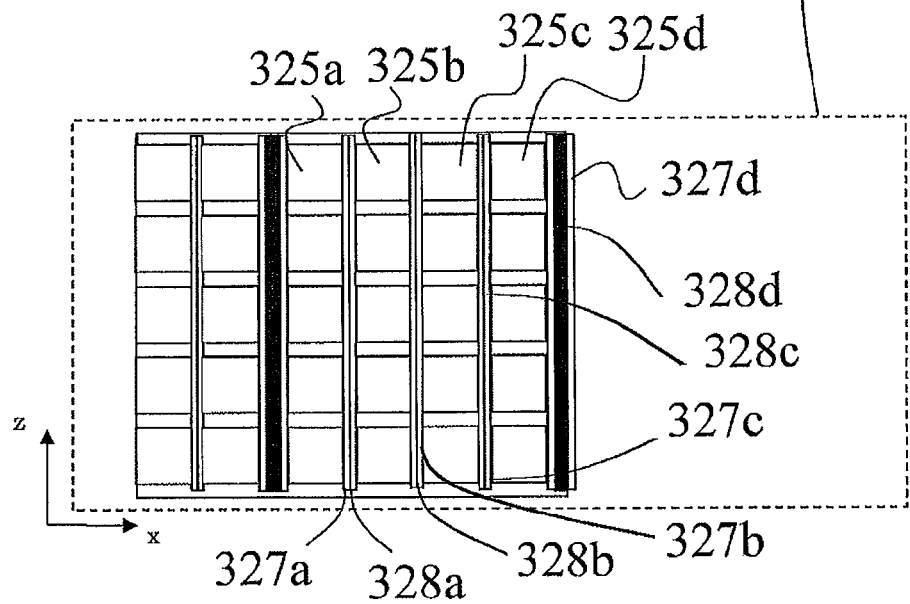

FIGS. 14A and 14B are views showing a configuration of an X-ray detector according to the third embodiment. The X-ray detector 321 shown in FIGS. 14A and 14B includes thick separators 327 provided every four separators and thick collimators 328 provided every four collimators. More specifically, of the separators 327a to 327d, the separators 327a to 327c become thin and only the separator 327d becomes thick. Moreover, of the collimators 328a to 328d, the collimators 328a to 328c become thin and only the collimator 328d becomes thick. Namely, the thicknesses of the separators 327 and the like are changed with four pitches.

As compared to the X-ray detector 321 (see FIGS. 2A and 2B) according to the first embodiment, the separator 327b and the collimator 328b become thick in FIGS. 2A and 2B while the separator 327b and the collimator 328b become thin in FIGS. 14A and 14B. The configuration shown in FIGS. 14A and 14B makes it possible to enhance the sensitivity, compared with the first embodiment and the second embodiment, because it has a number of places at which the thin separators are located.

Moreover, since addition method for signals outputted from the detection elements can be selected from the following, it becomes possible to carry out more flexible processing according to the resolution.

<Addition method 1> Signals of the photodiodes 326a, 326b, 326c, 326d are treated as independent signals, respectively (this corresponds to the high-resolution scanning mode in the first embodiment).

<Addition method 2> Signals of adjoining photodiodes 326a and 326b, and signals of adjoining photodiodes 326c and 326d, are added respectively.

<Addition method 3> All of signals of the photodiodes 326a to 326d are added (this corresponds to the high-sensitivity scanning mode in the first embodiment).

Therefore, in the third embodiment, the scanning mode in the image acquiring processing (see FIG. 3) is three in number corresponding to the addition methods 1 to 3 described above. When the addition method 1 or the addition method 2 is adopted, reconstruction processing of images is carried out according to the processing shown in FIG. 4. When the addition method 3 is adopted, reconstruction processing of images is carried out according to the processing shown in FIG. 5. Moreover, methods of the crosstalk correction, the scattered radiation correction and the position correction are changed according to the pitches of the detection elements and the thicknesses of the separators 327 and the collimators 328. Note that changes of the thicknesses of the separators 327 and the like are not limited to two pitches shown in the first embodiment or four pitches shown in the third embodiment, and are possible also with other pitches.

As described above, the X-ray CT device 100 according to the third embodiment makes it possible, in addition to the advantages obtained by the X-ray CT device 100 according to the first embodiment and the second embodiment, to improve the degree of freedom for sensitivity and resolution and to accommodate various examinations.

REFERENCE SIGNS LIST

100 X-ray CT device
200 Inputting means
300 Scanning means
310 X-ray generation unit
311 X-ray tube (X-ray source)
320 X-ray detection unit
321 X-ray detector
325a'~325f Scintillator (Detection element)
326a~326d Photodiode (Detection element)
327a'~327f Separator
328a~328f Collimator
330 Gantry
331 Bore
332 Rotating plate
340 Scanning control unit
400 Image generation unit (Image processing unit, Correction processing unit
500 Patient
501 Patient-carrying table

The invention claimed is:

1. An X-ray CT device provided with an X-ray source that irradiates a patient with X-rays, and an X-ray detector that detects the X-rays, the X-ray detector comprising:
a plurality of detection elements arrayed in a first direction; and
a plurality of separators that separate the detection elements arrayed in the first direction respectively from each other,
the separators each having a first-direction width which is a width in the first direction, first-direction widths of some separators each arrayed every predetermined number of separators being different from first-direction widths of the other separators.

2. The X-ray CT device according to claim 1, wherein
the X-ray detector further comprises collimators that restrict an incident direction of the X-rays to the detection elements, and wherein
the collimators are disposed on surfaces of the separators, the surfaces being on the side of the X-ray source, and first-direction widths of the collimators are different, corresponding to the first-direction widths of the separators disposed, every predetermined number of collimators.

3. The X-ray CT device according to claim 2, wherein
the collimators each have a predetermined height in a direction from the surfaces of the separators toward the X-ray source, and
heights of the collimators are different, corresponding to the first-direction widths of the separators.

4. The X-ray CT device according to claim 3, wherein
the separators having different first-direction widths every predetermined number of separators includes a first separator and a second separator having a smaller first-direction width than the first separator, and
the heights of the collimators satisfies condition defined by the following expression (1):

[Mathematical formula 1]

$$0.9 \times \frac{W_{327S} - W_{328S}}{W_{327L} - W_{328L}} H_{328L} \leq H_{328S} \leq 1.1 \times \frac{W_{327S} - W_{328S}}{W_{327L} - W_{328L}} H_{328S} \quad (1)$$

(Note that in the expression (1), $W_{327L}$ is a first-direction width of the first separator, $W_{328L}$ is a first-direction width of a collimator corresponding to the first separator, $W_{327S}$ is a first-direction width of the second separator, $W_{328S}$ is a first-direction width of a collimator corresponding to the second separator, $H_{328L}$ is a height of the collimator corresponding to the first separator, and $H_{328S}$ is a height of the collimator corresponding to the second separator).

5. The X-ray CT device according to claim 1, wherein the detection elements each have a constant first-direction width.

6. The X-ray CT device according to claim 1, wherein central positions in the first direction of the separators are located at equal spaces.

7. The X-ray CT device according to claim 2, wherein, in any separator of the plurality of separators, satisfied is a condition that a difference between the first-direction width of the first separator and the first-direction width of the collimator corresponding to the separator is within a range between 90% and 110% of a predetermined value.

8. The X-ray CT device according to claim 4, wherein the collimators have a place at which no collimator is disposed, corresponding to the first-direction widths of the separators, every predetermined number of collimators in the array.

9. The X-ray CT device according to claim 1, wherein the separators have different first-direction widths every one separator in the array.

10. The X-ray CT device according to claim 1, further comprising an image processing unit that, according to operation by an operator, regards respective X-rays detected by a plurality of detection elements every predetermined number of pitches, as X-rays detected by one detection element, and processes X-ray transmission image data.

11. The X-ray CT device according to claim 10, wherein
the first-direction widths of the separators take two values alternately, every predetermined number of separators in the array, and
the image processing unit regards respective X-rays detected by detection elements adjoining to a relatively thin separator, of the plurality of detection elements, as X-rays detected by one detection element.

12. The X-ray CT device according to claim 1, further comprising a correction processing unit that carries out at least one of crosstalk correction corresponding to a difference in the first-direction widths of the separators, scattered radiation correction corresponding to a difference in the first-direction widths of the separators, and position correction corresponding to a difference in the first-direction widths of the separators.

13. The X-ray CT device according to claim 1, wherein for the X-ray detector,
   some of the plurality of detection elements are arrayed also in a second direction different from the first direction,
   some of the plurality of separators are arrayed to separate the detection elements arrayed in the second direction respectively from each other,
   the separators that separate the detection elements arrayed in the second direction respectively from each other, each have a second-direction width which is a width in the second direction, second-direction widths of some separators each arrayed every predetermined number of separators being different from second-direction widths of the other separators.

14. The X-ray CT device according to claim 13, wherein second-direction widths of collimators which are disposed on surfaces of the separators that separate the detection elements arrayed in the second direction respectively from each other, the surfaces being on the side of the X-ray source, are different, corresponding to the second-direction widths of the separators disposed, every predetermined number of collimators.

15. The X-ray CT device according to claim 1, wherein the X-ray detector is configured with a plurality of detection modules arranged, in each of which the plurality of detection elements are arrayed.

* * * * *